(12) United States Patent
Eltem et al.

(10) Patent No.: US 9,551,012 B2
(45) Date of Patent: Jan. 24, 2017

(54) PRODUCTION OF TRICHODERMA CITRINOVIRIDE MICROPROPAGULES AS A BIOCONTROL AGENT BY MEANS OF AN ECONOMICAL PROCESS

(71) Applicants: Rengin Eltem, Izmir (TR); Sargin Sayit, Izmir (TR); Secil Sozer, Balikesir (TR); Fazilet Vardar Sukan, Izmir (TR)

(72) Inventors: Rengin Eltem, Izmir (TR); Sargin Sayit, Izmir (TR); Secil Sozer, Balikesir (TR); Fazilet Vardar Sukan, Izmir (TR)

(73) Assignee: T.C. EGE UNIVERSITESI, Izmir (TR)

( * ) Notice: Subject to any disclaimer, the term of this patent is extended or adjusted under 35 U.S.C. 154(b) by 30 days.

(21) Appl. No.: 14/649,214

(22) PCT Filed: Dec. 26, 2013

(86) PCT No.: PCT/TR2013/000379
§ 371 (c)(1),
(2) Date: Jun. 3, 2015

(87) PCT Pub. No.: WO2014/104998
PCT Pub. Date: Jul. 3, 2014

(65) Prior Publication Data
US 2015/0368673 A1    Dec. 24, 2015

(30) Foreign Application Priority Data
Dec. 28, 2012   (TR) .............................. a 2012 15621

(51) Int. Cl.
C12N 1/00         (2006.01)
C12Q 1/02         (2006.01)
C12P 1/02         (2006.01)
C12R 1/885        (2006.01)
A01N 63/04        (2006.01)
C12N 1/14         (2006.01)

(52) U.S. Cl.
CPC .................. *C12P 1/02* (2013.01); *A01N 63/04* (2013.01); *C12N 1/14* (2013.01); *C12R 1/885* (2013.01)

(58) Field of Classification Search
None
See application file for complete search history.

(56) References Cited

U.S. PATENT DOCUMENTS 5,330,912 A   7/1994   Toet et al.
5,422,107 A   6/1995   Kubota

FOREIGN PATENT DOCUMENTS

WO   WO2007094014 A1   8/2007
WO   WO2012093374 A2   7/2012

OTHER PUBLICATIONS

Hagn et al: "A new cultivation independent approach to detect and monitor common *Trichoderam* species in soils", Journal of Microbiological Methods, Elsevier, Amsterdam, NL, Mar. 28, 2007, pp. 86-92, vol. 69, No. 1, XP005928181.

(Continued)

*Primary Examiner* — Thomas J Visone
(74) *Attorney, Agent, or Firm* — Gokalp Bayramoglu

(57) ABSTRACT

The present invention relates to producing micropropagules from *Trichoderma citrinoviride* EGE-K-130 mold strain isolated from resources of our country and whose strain is molecularly identified, as a bio-control agent by means of an economical production process.

3 Claims, 1 Drawing Sheet

(56) References Cited

OTHER PUBLICATIONS

Antonio Evidente et al: "Citrantifidiene and Citrantifidiol: Bioactive Metabolites Produced by Trichoderma citrinoviride with Potential Antifeedant Activity toward Aphids", Journal of Agricultural and Food Chemistry, May 1, 2008, pp. 3569-3573, vol. 56, No. 10, XP055017184.

Prasad R D et al: "An improved medium for mass prodection of the biocontrol fungus Trichoderma harzianum", Indian Journal of Mycology and Plant Pathology, Society of Mycology and Plant Pathology, Udaipur,IN, Aug. 1, 2000, pp. 233-235, vol. 30, No. 2, XP001180737.

Punja Z K et al: "Using fungi and yeasts to manage begetable crop disease", Trends in Biotechnology, Elsevier Publications, Cambridge, GB, Sep. 1, 2003; pp. 400-407, vol. 21, No. 9, XP004450452.

Sargin Sayin et al: "Micropropagule production from Trichoderma harzianum EGE-K38 using solid-state fermentation and a comparative study for drying methods",Turkish Journal of Biology, pp. 139-146, vol. 37,No. 2, XP002721218.

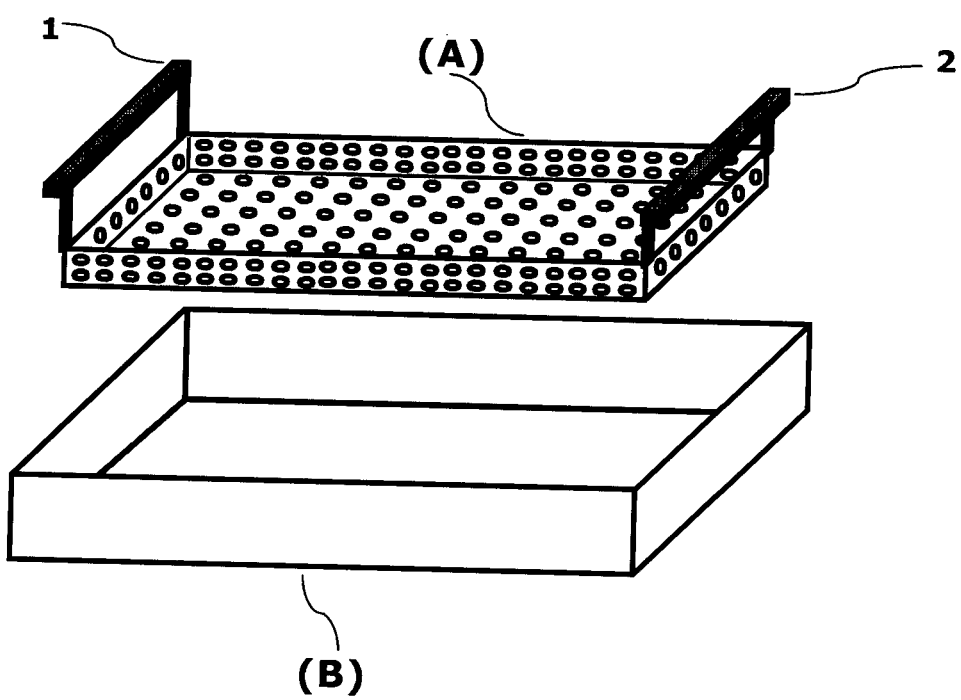

PRODUCTION OF TRICHODERMA CITRINOVIRIDE MICROPROPAGULES AS A BIOCONTROL AGENT BY MEANS OF AN ECONOMICAL PROCESS

TECHNICAL FIELD

The present invention relates to producing micropropagules from *Trichoderma citrinoviride* EGE-K-130 mould strain isolated from resources of our country and whose species is molecularly identified, as a bio-control agent by means of an economical production process.

The *Trichoderma citrinoviride* EGE-K-130 mould strain was deposited in National Center for Biotechnology Information, U.S. National Library of Medicine (8600 Rockville Pike, Bethesda Md., 20894 USA) on Aug. 20, 2012, and the Accession Number is JX125617.1. The definition of the strain is provided as follows: *Trichoderma citrinoviride* strain EGE-K-130 18S ribosomal RNA gene, partial sequence; internal transcribed spacer 1, 5.8S ribosomal RNA gene, and internal transcribed spacer 2, complete sequence; and 28S ribosomal RNA gene, partial sequence.

BACKGROUND

In our country, chemical methods are frequently used in the fight against agricultural diseases since they take effect in a short period of time and yield quick results. Pesticide use in Turkey has increased by 45% in the last 20 years. Pesticides are widely used especially in Mediterranean and Aegean regions of Turkey. Unconscious and uncontrolled use of pesticides has adverse effects on the environment and human health since they lead to development of persistence and residues in harmful microorganisms. Decrease or elimination of synthetic pesticide use in agriculture is desired. The most promising means to accomplish this goal is using new techniques based on biological control agents (BCAs) for disease control and, consequently, minimizing chemicals' detrimental effects on the environment.

Other methods, especially biological control, have been gaining prominence due to the fact that chemical control, one of the plant protection methods in agricultural production, has adverse effects on the environment and humans and that pathogens develop persistence against these. Biological control agents, including fungi, find a wide field of use along with bacteria (mainly *Bacillus thuringiensis*) since they have a wide spectrum in disease control, and owing, to their productive efficiency.

Fungi types such as *Trichoderma* spp., *Gliocladium* spp., *Aspergillus* spp., *Alternaria* spp., *Fusarium* spp., *Chaetomium* spp., *Ampelomyces* spp., *Coniothyrium* spp., Sporidosumun spp. and *Teretosperma* spp. provide significant antagonist effect. Moreover, *Trichoderma* species has a 50% share in fungal biological control agent market rather as a soil/growth enhancer which has led to more research being conducted on *Trichoderma* species.

Depending on the strain, *Trichoderma* use in agriculture provides numerous advantages. These advantages are: (i) biological control agent building colonies in rhizosphere allows it to settle quickly in constant microbial communities; (ii) pathogenic and competitive/harmful microflora is controlled by using various mechanisms; (iii) plant health is enhanced and (iv) root development is stimulated. As *Trichoderma* based biological control agents are compared with their counterparts (virus, bacteria, nematodes and protozoa), they come to the fore due to reasons such as enhancing plant growth and exhibiting high level of activity in remediation of soil.

The ultimate goal for production of any biological control agent is to implement the most economical mass production. Almost all bio-control agent products that are based on *Trichoderma* species contain spores as the active content.

This is associated with the physiological conditions of three microbial propagules (mycelia, conidia and chlamydospores) of *Trichoderma* species.

These three propagules have different physiological characteristics with regard to production, stability and bio-control agent activity. Thus, it is essential to choose propagules with the most suitable structures in order for *Trichoderma* species function as bio-control agents in an efficient manner.

Although exhibit perfect bio-control agent activity, mycelia, cannot survive downstream process steps such as drying and thus are not practical. Chlamydospores, on the other hand, require a 2-3 weeks period for cultivation and, although they are more persistent than mycelia, cannot survive drying process just like mycelia. As mentioned above, conidia are active bio-control agents, affected less by various environmental, conditions and may be produced in larger amounts in a much shorter period of 3-4 days. However, mycelia are inevitably present in the production environment along with conidia. Moreover, simultaneous production of mycelia ensures that there are various basic metabolites (e.g. antibiotics) for bio-control agent activity. For this reason, production of micropropagules containing conidia as lain propagules in addition to mycelia is the best strategy of producing *Trichoderma* species.

While commercial *Trichoderma* species preparations for biological control generally consist of bulk conidia, a good bio-control activity depends on fungus remaining vegetative, that is, being antagonistically active. For this reason, effective and efficient use of *Trichoderma* based biological control agents involves establishing a balance between formation of conidia at a very low cost during, production and drastic vegetative growth during use.

Commercial success of bio-control agents based on *Trichoderma* species also requires economically suitable biomass production processes (35-40% of production costs depends on raw material)

Despite its advantages, biomass production of *Trichoderma* based biological control agents is not very common, since high cost materials are used in production such as Mendelian conditions, molasses and corn steep liquor. The cost of such raw materials used in commercial production of biological control agents is the primary limiting factor. In order to overcome cost limitation, a number of researchers have successfully utilized dry corn fiber mass, sewage sludge compost and cranberry pulp. Despite use of alternative resources, production cost remains high due to the fact that these raw materials should be supported by other nutrients.

Growth and production are influenced by numerous parameters such as culture medium, inoculation, pH, temperature, oxygen and mass transfer. It is indicated that since filamentous fungi such as *Trichoderma* have various morphological structures, optimization and scaling of fermentation processes are difficult. Commercial production of conidia depends generally on manipulation of nutrients and substrata that support conidiation. Numerous studies have been conducted on optimal growth conditions for ensuring in vitro, conidia formation in many *Trichoderma* species. These studies have indicated that, in addition to medium pH, carbon and nitrogen conditions and C:N ratio are the primary environmental factors affecting conidia formation in *Trichoderma*. Although aerial spores (conidia) may be produced in solid media, in further phases of the process, large scale production of conidia becomes difficult due to the fact that optimal temperature and ventilation values cannot be maintained. It is known that liquid fermentation is used for chlamydospores production. However, not every fungus has the capability of producing spores in deep culture. For this reason, production conditions should be optimized specifically for the chosen species in order to obtain maximum propagule yield.

For mass production of a biological agent by means of solid culture fermentation, a very large amount of spore biomass is required. Substrates such as grains, unsieved coarse flour, brans, hay, plant residues and organic fertilizers are used for mass production of *Trichoderma harzianum*. Pulp residue (even used pulp residue) is a suitable support substrate for solid culture fermentation. Wine pulp contains various nutrients for microbial growth such as carbon resource, nitrogen resource and trace elements. Such wine wastes are substantially inexpensive substrates and are suitable for solid culture fermentation. Moreover, other agricultural-industrial wastes such as solid paper wastes and cellulosic plant residues from paper factories are released to the environment every year, increase pollution and lead to waste disposal problems. For this reason, in line with the need for large scale low cost production of environmentally friendly bio-pesticides, studies for regionally available more inexpensive substrates are being conducted for mass production of *T. harzianum*.

Although there are no patents in the field related to *Trichoderma citrinoviride* strain, there are patents that covers production of *Trichoderma harzianum* conidia which is of the same genus and whose patent subject matter relates to production, namely U.S. Pat. No. 5,330,912 A 19940719, U.S. Pat. No. 5,422,107 A 19950606 and WO 2007/094014 A1 20070823.

SUMMARY OF THE INVENTION

The present invention includes the production medium and production technique suitable for production of *Trichoderma citrinoviride* EGE-K-130 micropropagules in an economical manner and in large quantities. It relates to obtaining laboratory scale active, biomass with high efficiency by solid culture fermentation for the subject matter of the patent, production of *Trichoderma citrinoviride* micropropagules as a bio-control agent by means of an economical process.

In such production, for solid culture fermentation production of *Trichoderma citrinoviride* EGE-K-130 mould strain propagules whose species is molecularly identified, mycoparasitic activity, lytic enzyme activities, optimal reproduction and optimal sporification temperature, light effect, optimal carbon and nitrogen resources, optimal initial humidity value and pH value of the strain are determined.

For production of *Trichoderma citrinoviride* EGE-K-130 strain under the determined optimal conditions in a perforated tray system certain amount of substrate (carbon and nitrogen resources) is placed on the trays.

The initial humidity and pH value of the medium is adjusted. It is sterilized at 121° C. for 30 minutes in an autoclave.

After sterilization, inoculation material is prepared with spores from *Trichoderma citrinoviride* EGE-K-130 strain and inoculated into the production media on the trays.

The trays are incubated under the optimal production temperature and light intensity. Samples are taken from the trays during incubation and modified microbial counting methods are utilized for determining the number of micropropagules.

Micropropagule numbers are expressed in colony forming unit per one gram of substrate used (cfo/g solid substrate).

BRIEF DESCRIPTION OF THE DRAWING

FIG. 1 is a perspective view of trays used in production according to the invention. Definitions of References in the FIGURE, A) Perforated timer tray (1), (2) Handles for carrying and placing inner tray B) Outer tray in which the perforated tray is placed.

DETAIL DESCRIPTION OF THE INVENTION

In FIG. 1, the invention is production of micropropagules as a bio-control agent from *Trichoderma citrinoviride* EGF-K-130 (GenBank Accession number: JX125617.1) isolated from timber wastes and Whose strain is molecularly identified, in the most economical manner and in large amounts via solid culture fermentation technique by placing an inner tray (A) made of stainless steel and having perforations on the bottom and sides for ventilating the production medium positioned within into an outer tray (B) also made of stainless steel so as to be able to keep the optimal initial humidity of the substrate, which comprises the following process steps:

performing preparations including placement of certain amount of solid substrate on trays, initial humidity and pH adjustments for micropropagule production in trays preparing inoculation for production in trays;

producing propagules in trays under appropriate conditions;

micropropagule numbers in trays during, and after production.

In the step of performing preparations for production of the said mould strain micropropagules in trays, a production medium of a total 200-300 g (such as 250 g) containing 1-10% (such as 3%) malt grass and 80-99% (such as 95%) wheat bran by weight is adjusted to an initial humidity ratio in a range of 60-75% (such as 70%), the initial pH value is adjusted to a certain value in the range of 4.00-6.00 (such as pH 5.00) with a 5NHCl solution, solid medium is dispersed onto the perforated inner tray (A), perforated inner tray is held by the handles (A(1) and A(2)) and is placed into the outer tray (B) followed by sterilization at 121° C. for 30 in an autoclave.

In the step of preparing inoculation for production of the said mould strain micropropagules in trays, spores are multiplied in potato dextrose agar (MA), a spore suspension at a certain amount such as $1.0 \times 10^8$ spore/ml is prepared and inoculated into the production media on the tray.

In the step of producing the said mould strain micropropagules in trays under appropriate conditions, the trays are placed on shelves in a temperature controlled and lighted room and micropropagules are produced under a certain light intensity in the range of 50-80 lux (such as 55 lux) and at a certain temperature in the range of 25-35° C. (such as 28° C.) for 3-7 days (such as 5 days).

In the step of determining micropropagule numbers in trays during and after production of, 10 sections of samples collected from the production medium is mixed with distilled water, homogenized for a certain period in the range of 500-800 seconds (such as 600 seconds) in a homogenizer, the collected samples are successively diluted with distilled water containing Tween 80 and formed colonies are counted by means of the pour plate method in petri dishes containing dichloranglycerol (DG-18) agar.

The invention claimed is:

1. A process for preparing micropropagules as a biocontrol agent from *Trichoderma citrinoviride* EGE-K-130 mould strain isolated from timber wastes in a plurality of trays, wherein the trays include an inner tray and an outer tray, both made of stainless steel, and the inner tray includes perforations on a bottom and sides of the inner tray, the process comprising:
  adjusting an initial humidity ratio of solid media to be in a range of 60-75%, wherein the media is provided at an amount of 200-300 g, including 1-10% malt grass and 80-99% wheat bran by weight;
  adjusting the initial pH value of the media to be in the range of 4.00-6.00, using a 5NHCl solution;
  dispersing the solid media onto a perforated inner tray;
  holding the perforated inner tray by the handles;
  placing the perforated inner tray into the outer tray;
  sterilizing at a temperature of 121° C. for 30 minutes in an autoclave;
  multiplying a plurality of spores in potato dextrose agar (PDA);
  preparing a spore suspension at an amount of $1.0 \times 10^2$ spores/ml;
  inoculating the spore suspension into the media;
  producing the micropropagules on the inner tray;
  determining micropropagules quantity during and after the process.

2. The process according to claim 1, step of producing the micropropagules on the inner tray further comprising:
  placing the trays on a plurality of shelves in a room with a controlled temperature and light; and
  producing micropropagules for 3-7 days, under a light intensity in the range of 50-80 lux and at a temperature in the range of 25-35° C.

3. The process according to claim 2, a step of determining micropropagules quantity during and after the process further comprising:
  mixing ten samples collected from the media with distilled water;
  homogenizing for a period in the range of 500-800 seconds in a homogenizer;
  diluting the samples with distilled water containing Tween 80; and
  counting a plurality of formed colonies by a pour plate method in petri dishes including dichloranglycerol (DG-18) agar.

* * * * *